United States Patent [19]

Krabetz et al.

[11] 4,052,450

[45] Oct. 4, 1977

[54] CATALYTIC OXIDATION OF α-OLEFINS

[75] Inventors: Richard Krabetz, Kirchheim; Heinz Engelbach, Limburgerhof; Ulrich Lebert, Ludwigshafen; Walter Frey, Manheim; Gerd Duembgen, Dannstadt; Fritz Thiessen; Carl-Heinz Willersinn, both of Ludwigshafen, all of Germany

[73] Assignee: BASF Aktiengesellschaft, Ludwigshafen, Germany

[21] Appl. No.: 405,152

[22] Filed: Oct. 10, 1973

[30] Foreign Application Priority Data

Oct. 12, 1972 Germany .............................. 2249922

[51] Int. Cl.² ............................................. C07C 51/32
[52] U.S. Cl. ................................. 260/533 N; 252/432; 252/435; 252/437; 252/462; 252/464; 252/465; 260/413; 260/465.3; 260/604 R
[58] Field of Search ....................... 260/533 N, 604 R

[56] References Cited

U.S. PATENT DOCUMENTS

| | | | |
|---|---|---|---|
| 3,576,764 | 4/1971 | Yamaguchi et al. | 260/533 N |
| 3,595,910 | 6/1971 | Ball | 260/530 N |
| 3,642,930 | 2/1972 | Grasselli et al. | 260/533 N |
| 3,708,434 | 1/1973 | Eden | 260/533 N |
| 3,716,496 | 2/1973 | Yoshino | 260/604 R |
| 3,761,424 | 9/1973 | Koberstein et al. | 260/533 N |
| 3,786,000 | 1/1974 | Ono et al. | 260/604 R |
| 3,799,978 | 3/1974 | Ohara et al. | 260/533 N |
| 3,825,600 | 7/1974 | Ohara et al. | 260/533 N |

*Primary Examiner*—Vivian Garner
*Attorney, Agent, or Firm*—Keil, Thompson & Shurtleff

[57] ABSTRACT

In the oxidation of α-olefins in the gas phase to α,β-olefinically unsaturated aldehydes and carboxylic acids with molecular oxygen in the presence of an inert gas using a catalyst containing molybdenum and bismuth with elements as oxides or mixed oxides at from 280° to 450° C a content of indium and/or aluminum and/or lanthanum and/or gallium as oxide or mixed oxide results in an improvement in the conversion and/or activity and/or life of the catalyst.

17 Claims, No Drawings

CATALYTIC OXIDATION OF α-OLEFINS

It is known from many literature references that α-olefins such as propylene and butenes can be oxidized catalytically in the gas phase with molecular oxygen to the corresponding α,β-olefinically unsaturated aldehydes and/or carboxylic acids, for example acrolein and/or acrylic acid when using propylene. When this process is carried out in the presence of ammonia, the corresponding nitriles, for example acrylonitrile or methacrylonitrile, are usually obtained instead of the α,β-olefinically-unsaturated carbonyl compounds.

Suitable catalysts which have been known for a long time are those based on molybdenum and bismuth in the form of compounds containing their oxides or mixed oxides; these generally contain, in addition to a preponderant amount of molybdenum, a minor amount of bismuth and usually at least one other element — usually metal — or oxide or mixed oxide of the same or both.

For example, a catalyst for the oxidation of α-olefins to the corresponding aldehydes which is based on bismuth molybdate and has been modified with copper is known from German Published Application (DOS)No. 1,542,457. This catalyst, however, leaves much to be desired especially as regards the conversion achievable therewith in the oxidation of propylene or butene and also the space-time yields of, for example, acrolein.

Catalysts for the oxidation of α-olefins to the corresponding aldehydes and acids which contain, in addition to predominant amounts of molybdenum, minor amounts of bismuth and also iron and phosphorus are disclosed in German Published Application No. 1,225,901 and British Pat. Nos. 822,140 and 903,034. The disadvantage of these prior art catalysts are in particular low abrasion resistance and poor selectivity in conversions of more than 50 to 60 mole%.

Catalysts containing additional elements (particularly metals) disclosed in German Published Applications Nos. 2,000,425, 2,020,791, 2,125,032, 1,593,186, 1,792,424, and 2,049,583 generally give better conversions and exhibit improved selectivity with short residence times or less than two to four seconds using small amounts of steam (less than 10 to 20% by volume based on the gas passed over the catalyst), but even here either the selectivity and conversion leave much to be desired or the activity of such prior art catalysts often subsides very rapidly under the operating conditions, particularly in the case of systems containing alkali. German Published Application No. 2,000,425 relates to catalysts of the general formula $Ni_aFe_bBi_cMe_d$—$Mo_eO_f$, in which Me denotes Ti, Ge, Sn, B or Cr, $a$ is 1.2 to 18, $b$ is 0.12 to 6, $c$ is 0.12 to 6, $d$ is 0.12 to 6 and $e$ is 12.

German Published Application No. 2,020,791, which relates to a method for the catalytic gas phase oxidation of α-olefins to the corresponding α,β-olefinically unsaturated carbonyl compounds which is an improvement over the methods of German Published Applications Nos. 1,268,609 and 1,667,209, discloses a catalyst of the general formula: $Ni_aCO_bFe_cBi_dL_eM_fMo_gO_h$, in which L is P, As or B, M is K, Rb or Cs, $a$ and $b$ are each zero to 15 and together 2 to 15, $c$ is 0.5 to 7, $d$ is 0.1 to 4, $e$ is zero to 4, $f$ is 0.01 to 0.5, $g$ is 12 and $h$ is 35 to 85.

The catalysts used in the process of German Published Application No. 2,125,032 have the general formula: $Co_aFe_bBi_cW_dMo_eSi_fZ_gO_h$ in which Z is Li, Na, K, Rb or Cs, $a$ is 2 to 20, $b$ and $c$ are each 0.1 to 10, $d$ is 0.5 to 10, $e$ is 2 to 11.5, $f$ is 0.5 to 15 and $g$ is 0.005 to 1.0, the sum of $d$ and $e$ being 12.

The catalysts used in the process of German Printed Application (DAS) No. 1,593,186 have the general formula: $Ni_aCo_bFe_cBi_dAs_eP_fMo_gO_h$ in which $a$ and $b$ are each zero to 3, $f$ is zero to 20 and together 0.5 to 20, $c$ is 0.5 to 8, $d$ is 0.1 to 7, $e$ is zero to 2, $g$ is 12 and $h$ is 36 to 98, $f$ being less than 0.1 when $e$ is zero.

Finally, the catalysts used in the methods of German Published Applications Nos. 1,792,424 and 2,049,583 for the catalytic gas phase oxidation of α-olefins to mixtures of the corresponding carbonyl compounds have the general formula: $Ni_aCo_bFe_cBi_dP_eMo_fO_g$ in which $a$ is zero to 20, $b$ is zero to 15, $c$ is 0.1 to 7, $d$ is 0.1 to 4, $e$ is 0.1 to 2, $f$ is 12 and $g$ is 35 to 85, the sum of $a$ and $b$ being 2 to 20. In these prior art catalysts there are used additions of from 0.2 to 5%, particularly from 0.5 to 2%, by weight (based on the catalyst) of samarium or tantalum and also silicon dioxide and/or sheet-silicate as carrier.

An object of the present invention is to improve conventional catalysts based on molybdenum and bismuth and processes carried out therewith for the oxidation of α-olefins in the gas phase to the corresponding α,β-olefinically unsaturated aldehydes and acids. A further object of the invention is in particular to improve the conventional method of oxidizing propylene in the gas phase using conventional catalysts based on molybdenum and bismuth to acrolein and also acrylic acid.

We have now found that the oxidation of α-olefins with molecular oxygen in the presence of an inert gas and in the presence of absence of steam and/or ammonia at temperatures of from 280° to 450° C on a conventional catalyst which is based on molybdenum and bismuth and which contains these elements with other elements as oxides or mixed oxides to form the corresponding, β-α-olefinically unsaturated aldehydes can be advantageously carried out by using a catalyst containing molybdenum and bismuth which additional contains a small amount of indium and/or lanthanum and/or aluminum and/or gallium as an oxide or mixed oxide.

α-Olefins having three or four carbon atoms such as propylene, butene-1, butene-2 (which is readily isomerized to butene-1 in accordance with the thermodynamic equilibrium over the catalysts according to the invention) and isobutylene are of particular interest, propylene being preferred. In general suitable olefins are those having the general formula:

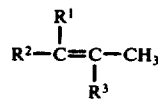

where
R¹ is hydrogen or alkyl of one to six carbon atoms;
R² is hydrogen or methyl; and
R³ is hydrogen or methyl,
or their double bond isomers.

For the process there are used conventional catalysts based on molybdenum and bismuth oxides or mixed oxides which have been modified with a small amount of indium and/or lanthanum and/or aluminum and/or gallium in the form of an oxide or mixed oxide of such element and which may additionally contain other elements or their oxides or mixed oxides such as are conventionally used in catalysts based on oxides of molybdenum and bismuth. Such catalysts as a rule have the general formula:

$$Mo_aBi_bMe^1_cMe^2_dMe^3_eMe^4_fMe^5_gO_h \tag{I}$$

where

- Me¹ is indium and/or gallium and/or lanthanum and/or aluminum, preferably indium and/or lanthanum;
- Me² is iron and/or copper, preferably iron;
- Me³ is nickel and/or cobalt, preferably nickel;
- Me⁴ is one or more elements selected from the group: phosphorus, boron, arsenic, chromium, vanadium and tungsten, advantageously from the group P, W and Cr and preferably combinations of P with W or Cr with W;
- Me⁵ is one or more metals selected from the group: Ag, Pb, Mn, Re, Sn, Ge, Sm, Nb, Ta, Mg, Ca, Sr, Ba and Be, preferably from the group Mn, Re, Sn and Ge; $a$ is 12;

$b$ is 0.1 to 6, preferably 0.5 to 3;

$c$ is 0.005 to 3, advantageously 0.01 to 2 and preferably 0.01 to 1;

$d$ is 0.1 to 8, advantageously 0.3 to 6 and preferably 0.5 to 3;

$e$ is zero to 16, advantageously 4 to 12 and preferably 6 to 11;

$f$ is zero to 6, advantageoulsy 0.1 to 5 and preferably 0.2 to 3;

$g$ is zero to 3, advantageously 0.05 to 2 and preferably 0.1 to 1; and $h$ is 36 to 102, preferably 41 to 84.

Even in the simple forms:

$Mo_aBi_bMe^1_cMe^2_dO_h$ (Me² being for example Cu and/or Fe) (formula II)

$Mo_aBi_bMe^1_cMe^2_dMe^4_fO_h$ (Me² being for example Fe and Me⁴ for example P) (formula III)

the content of indium and/or lanthanum and/or aluminum and/or gallium results in particular in an increase in yield in the oxidation of propylene, for example as compared with the method of German Published Application No. 1,542,457 in which bismuth molybdate modified with copper is used as catalyst or the method according to German Printed Application No. 1,947,830, Example 5, in which FeBiPMoO catalysts are used.

The parameters Me¹, Me² and Me⁴ and also $a, b, c, d$ and $f$ in the general formulae (II) and (III) have the same meanings as in formula (I). $h$ in formula (II) is 36 to 58 and in formula (III) 36 to 76.

Those catalysts of the general formula (I) are of particular interest in the new process in which Me² is Fe or Fe and Cu, $d$ is 0.1 to 6 and preferably 0.5 to 3, Me³ is Ni or Co, $e$ is four to twelve and particularly 6 to 10 and $h$ is 40 to 96 (general formula IV). Such catalysts have better selectivity than those of general formulae (II) and (III) and therefore make possible, as compared with the methods of German Printed Application No. 1,125,901 and British Pat. Nos. 822,140 and 903,034, high reaction temperatures particularly at short residence times of 2 to 4 seconds and increased yields of desired products, particularly acrolein, especially when small amounts of steam which are less than 10 to 20% by volume based on the total volume of reaction gas are present.

Catalysts of the general formula (I) exhibit improved selectivity and a longer life when Me² is Fe or Fe + Cu, $d$ is 0.5 to 3, Me³ is Ni or Ni + Co, $e$ is 4 to 12, Me⁴ is P and/or W and/or Cr, $f$ is 0.1 to 5, preferably 0.2 to 3, and $h$ is 41 to 87 (general formula (V)). Moreover, such catalysts, which have a longer life than catalysts which do not contain any Me⁴, have the advantage over comparable prior art catalysts as disclosed for example in German Published Applications Nos. 2,049,583, 1,792,424 and 2,020,791 and in German Printed Application No. 1,593,186 of an increased conversion to the desired product in a short residence time, particularly when small amounts of steam of from about 10 to 20% by volume are present in the reaction gas, especially in the oxidation of α-olefins to the corresponding α,β-olefinically unsaturated aldehydes, for example of propylene to acrolein.

Similar favorable conversions at high selectivity are obtained in the new process with catalysts of the general formula (I) in which Me² is Fe and $d$ is 0.5 to 3; Me³ is Ni or Ni + Co; $e$ is 4 to 12; Me⁴ is W and/or Cr and/or P, preferably W + P or W + Cr; $f$ is 0.1 to 5 and preferably 0.2 to 3; Me⁵ is Sn, Ge, Mn, Re; $g$ is 0.05 to 2 and preferably 0.1 to 1; $h$ is 41 to 84 and preferably 41 to 76 (general formula (VI)). These catalysts also have the abovementioned advantage over catalysts disclosed in German Published Application No. 2,125,032. Moreover, particularly as compared with systems containing alkali, the activity of the catalysts used in the process according to the invention declines very slowly in the course of the oxidation of propylene and isobutylene. Finally, those catalysts may be used in the new process which additionally contain other elements (Me⁵) in the form of their oxides and/or mixed oxides; examples of these are Sm, Nb and Ta.

These catalyst components generally do not have any detrimental effect on the activity and selectivity of the catalyst. In many cases they are of advantage, particularly Mn and Re. To sum up, then catalysts derived from the formula (I) may be represented by the following general formulae:

 (II)

 (III)

 (IV)

 (V)

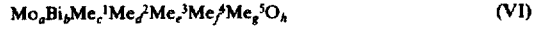 (VI)

in which Me¹, Me², Me³, Me⁴, Me⁵ and $a, b, c, d, e, f, g$ and $h$ have the above meanings. Catalysts of the general formulae (IV), (V) and (VI) are preferred, those of general formulae (V) and (VI) in which Me¹ is indium and/or lanthanum being particularly preferred.

The catalysts may be prepared by conventional methods. For example compounds of the components of the catalyst which are capable of being converted into oxides upon heating may be evaporated in a solvent, particularly in water, dried and calcined, generally in the air at a temperature of from about 180° to 300° C and preferably at from 200° to 260° C. The material may be shaped and then recalcined for example At 350° to 800°, preferably at from 400° to 650° C. Molybdenum is generally used, and also tungsten and vanadium if desired, in the form of the ammonium salt, and the remaining components may be used for example as nitrates, oxalates, formates, tartrates, chlorides, sulfates or as oxyacids, for example boric acid, phosphoric acid and arsenic acid.

The active catalyst material may also be prepared by evaporating ammonium salts of the acid catalyst components, for example of molybenum, and then kneading the product with metal salts of the said type, if necessary shaping the product and calcining it.

The active catalyst material may be used as such in which case for example a small amount, generally from about 0.5 to 15% by weight (based on the active material) of lubricant such as graphite or resin, for example a polymerized hydrocarbon, may be added which in the oxidative aftertreatment of the material at temperatures of from 200° to 800° C is decomposed into gaseous products so that the catalyst becomes porous.

The active catalyst material may also be applied to conventional carriers, for example diatomite, finely divided silicic acid, synthetic and/or natural sheet-silicates such as montmorillonite, bentonite and steatite, and also to silicon carbide, aluminum silicates, highly calcined aluminum oxides, zirconium oxides, titanium oxides or in some cases to metallic aluminum or may contain such carrier material as diluents generally in amounts of up to about 80% by weight, preferably of up to 50% by weight. As carrier materials and for diluting the catalysts silicic acid and/or silicates are preferred, if desired in the form of extrudates or spheres.

The novel process is generally carried out at temperatures of from 280° to 450° C, a mixture of the α-olefin, molecular oxygen and inert gas with or without steam being passed over the catalyst. The temperature range from 300° to 420° to particular interest, temperatures of from 320° to 400° C being particularly preferred. The residence time of the gas mixture in contact with the catalyst is generally only a few seconds, for example less than twenty seconds, and is usually from 0.05 to 6, advantageously from 0.1 to 4, and preferably from 0.5 to 3 seconds. The pressure conditions are those conventionally used in the oxidation of α-olefins with such catalysts.

The gas mixtures oxidized over the new catalysts may have the conventional composition. The content of α-olefin, for example propylene or isobutylene, is generally from 0.5 to 15% by volume preferably from 2 to 6% by volume, if the oxygen is supplied in the form of air and from 6 to 15% by volume if pure oxygen is used, part of the reaction gas after separation of acrylic acid being added to the gas mixture supplied to the oxidation (recycle gas method). The oxygen concentration is usually from 2 to 20, preferably from 5 to 15%, by volume. The mixture contains inert gases such as carbon monoxide, carbon dioxide and nitrogen and possibly, usually in minor amounts, rare gases, hydrogen, ethylene and propane. The synthesis gas may also contain steam. The amount of steam may generally be up to about 40% by volume but an amount of less than 20%, advantageously less than 10% and particularly from 2 to 8% by volume is preferred. Since the reaction gas obtained in the process of oxidation of α-olefins (after separating as much as possible of the desired reaction products, for example acrolein, acrylic acid and possibly byproducts) is generally supplied together with makeup gas (air or oxygen, α-olefin and if desired ammonia) to the reactor as synthesis gas, the synthesis gas generally contains other substances which are gaseous under the reaction conditions, particularly acrolein, methacrolein, acrylic acid, methacrylic acid, maleic acid, acetic acid, formaldehyde, acetone, acetaldehyde, and the like and also traces of solvent or extractant which have been entrained in the recycled reaction gas in the separation of the desired products. The amount of these substances, for example acrolein, may be up to 10% by volume, for example 3% by volume. The percentages by volume refer to the gas composition at 20° C and atmospheric pressure.

The reaction mixture in the novel process may be worked up by a conventional method and the desired reaction products, for example acrolein, methacrolein and any acrylic acid or methacrylic acid may be separated for example by extraction.

In the preferred embodiment propylene is reacted over the catalyst according to the invention and the reaction mixture in the gaseous state, if desired after having been mixed with air or oxygen, is passed over a second catalyst which is selective for the further oxidation of acrolein to acrylic acid. After the acrylic acid has been washed out and the condensable products have been separated, part of the off gas may be advantageously recycled to the synthesis.

The invention is further illustrated by the following Examples in which parts and percentages are by weight.

EXAMPLE 1

Oxidation of propylene

The following aqueous solutions are prepared:

A. 211.8 parts of ammonium heptamolybdate hydrate $(NH_4)_6Mo_7O_{24}.4H_2O$ is dissolved in 200 parts of water at below 50° C and 11 parts of 85% aqueous phosphoric acid is added.

B. 1.35 parts of ammonium paratungstate is suspended in solution (A).

C. 243 parts of nickel nitrate hexahydrate, 8.7 parts of cobalt nitrate hexahydrate and 81 parts of ferric nitrate nonahydrate are dissolved in 300 parts of water.

D. 8 parts of indium chloride is dissolved in 20 parts of water.

E. 48.7 parts of bismuth nitrate pentahydrate is dissolved in 72 parts of 17% aqueous nitric acid.

Solutions (A), (B), (C) and (D) are introduced in any sequence into a stirred vessel and a mixture of 95 parts of montmorillonite and 32 parts of finely divided silicon dioxide (particle size from 4 to 20 microns) which has been calcined for 5 hours at 1000° C is added. Solution (E) is then added and the whole is mixed for about an hour. The material obtained is dried for about two hours at 250° C and then calcined for about twenty minutes at 580° C in a stream of air. The product is comminuted by a conventional method and a fraction is separated having a particle size of from 2 to 4 mm by sieving. This fraction is used as a catalyst.

30 ccm of the catalyst is placed in a steel tube having an internal diameter of 15 mm and the filled steel tube is heated to 390° C in a salt bath. A mixture of 3.3 liters of propylene, 40 liters of air and 26 liters of nitrogen which has been saturated with water vapor at about 30° C (content of water vapor; 4% by volume) in then passed per hour through the steel tube and over the catalyst.

The residence time is 1.35 seconds. The conversion of propylene in the reaction is 87 mole%, the yield of acrolein is 74 mole% and the yield of acrylic acid 4 mole%. 9 mole% of the propylene is oxidized to carbon dioxide, formaldehyde, acetic acid and maleic acid. The selectivity of the catalyst with reference to the formation of acrolein and acrylic acid is a total of 90 mole%.

EXAMPLES 2 to 14

Oxidation of propylene

Various catalysts whose composition is given in atomic ratios in the following Table 1 are prepared as described in Example 1. This Table also indicates the conditions under which calcination is carried out.

Propylene is then oxidized with the catalysts in the manner described in Example 1. The salt bath temperature used in each case, the conversion of propylene achieved, the yields of acrolein and acrylic acid and the selectivity of the catalyst are also given in the following Table 1. Propylene conversion, yields of acrolein and acrylic acid and selectivity are given in mole%.

Comparative experiments (Examples 2a, 4a and 7a) are carried out and these show that under comparable conditions there is an improvement in the properties of the molybdenum-bismuth catalysts when indium is present. The results are given in the following Table 1a.

EXAMPLES 18 to 29

Oxidation of propylene

The catalysts used in these Examples are prepared as described in Example 1 except that any Pb, Ag, Sn, Cr, Al and Mn used as additional components are used as nitrates and Ge as tetrachloride together with the nickel solution, V is used as ammonium metavanadate and arsenic and boron are used as arsenic or boric acid with the molybdate and 250 parts of a 25% aqueous silica sol solution (instead of the aerosil-montmorillonite mixture) is used as carrier (F).

Apart from this, the procedure of Example 1 is followed. The exact composition of the catalysts, the calcination temperature and the calcination period used in the preparation of the catalysts, the conversion of propylene and the selectivity of the catalysts are given in the following Table 2.

EXAMPLE 30

Oxidation of propylene to acrylic acid 25 ml of the catalyst prepared according to Example 15 is placed in a stainless steel tube having a diameter of 15 mm and heated to a bath temperature of 370° C. A mixture of 3300 ml of propylene, 33,000 ml of air and 26,000 ml of nitrogen is passed per hour over the catalyst. The hot reaction mixture is cooled to 275° C and passed over 25 ml of a catalyst which has been prepared according to Example 1 of German Pat. No. 1,908,965 and which is selective for the oxidation of acrolein to acrylic acid. According to analysis of the discharge 90 mole% of propylene is converted, the yield of acrylic acid, based on propylene used, is 6.5 mole%, the selectivity of acrylic acid formation is 72 mole% and the space-time yield is 138 g of acrylic acid per liter of catalyst per hour.

EXAMPLE 31

Oxidation of propylene

A catalyst of the general formula:

$Mo_{12}Bi_1In_{0.4}Fe_{1.2}Ni_8W_{0.5}Sn_{0.6}Cr_{1.2}O_{51.8}$ is prepared as described in Example 1, tungsten being used in the form of ammonium paratungstate, tin in the form of stannous chloride dihydrate and chromium in the form of chromium nitrate nonahydrate. The catalyst is dried and calcined as described in Example 1. Propylene is then oxidized as described in Example 1 at a bath temperature of 350° C. The conversion of propylene is 89 mole%, the yield of acrolein 74 mole%, the yield of acrylic acid 6 mole% and the selectivity 90 mole%. After periods of operation of 12 hours and 72 hours there is no appreciable change in the propylene conversion or the yield of acrolein or acrylic acid.

EXAMPLE 32

A catalyst of the general formula:

$Mo_{12}Bi_1In_{0.4}Fe_2Ni_8Co_{0.3}W_{0.1}P_1O_{52.2}$ is prepared as described in Example 1 and used as described in Example 1 for the oxidation of propylene. Temperatures, reaction periods and results are given in Table 3.

Comparative experiment using catalyst of German Published Application No. 2,049,583

A catalyst of the composition:

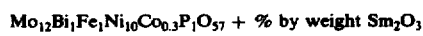
$Mo_{12}Bi_1Fe_1Ni_{10}Co_{0.3}P_1O_{57}$ + % by weight $Sm_2O_3$ is prepared as described in Example 1 of the said application and used for the oxidation of propylene as described in Example 1 hereof. The results obtained after various periods and the bath temperatures used may be seen from Table 4.

Comparison of the results given in Tables 3 and 4 shows that under comparable conditions the activity of the catalysts according to this invention is not adversely affected over relatively long periods of operation in contrast to that of the prior art catalyst.

Comparative experiment using catalyst of German Published Application No. 2,125,032

A catalyst of the general formula:

$M_{10}Bi_1Fe_1Co_4W_2K_{0.06}Si_{1.35}O_{45.7}$ is prepared as described in Example 1 of the said application and used for the oxidation or propylene as described in Example 1 hereof. At a bath temperature of 370° C the propylene conversion after 30 hours is 63 mole%, the yield of acrolein 46 mole%, the yield of acrylic acid 5 mole% and the selectivity 81 mole%. The values change after an on-stream period of 73 hours, in spite of a constant increase in the bath temperature to 410° C, to only 69 mole% of propylene conversion, 43 mole% of acrolein and 6 mole% of acrylic acid so that the selectivity has declined to 71 mole%.

TABLE 1

| | Composition of Catalyst | | 1 | 2 | 3 | 4 | 5 | 6 | 7 |
|---|---|---|---|---|---|---|---|---|---|
| 2 | $Mo_{12}Bi_1In_{0.8}Fe_1Ni_{10}O_{50.2}$ | | 4 hrs. 486° C | 370 | 91 | 64 | 13 | 77 | 85 |
| 3 | $Mo_{12}Bi_1In_{1.6}Fe_1Ni_{10}O_{51.4}$ | | 4 hrs. 486° C | 360 | 89 | 62 | 4 | 66 | 74 |
| 4 | $Mo_{12}Bi_1In_{0.4}Fe_{1.2}Co_5W_4O_{56.9}$ | | 6 hrs. 470° C | 350 | 87 | 39 | 26 | 65 | 75 |
| 5 | $Mo_{12}Bi_1In_{1.6}Fe_{1.2}Co_5W_4O_{58.7}$ | | 6 hrs. 470° C | 360 | 89 | 62 | 4 | 66 | 74 |
| 6 | $Mo_{12}Bi_1In_{0.4}Fe_1Ni_{10}Co_{0.3}P_1O_{52.4}$ | | 10 min. 650° C | 360 | 90 | 72 | 5 | 77 | 86 |
| 7 | $Mo_{12}Bi_1In_{0.1}Fe_1Ni_{10}Co_{0.3}P_1O_{52}$ | | 10 min. | 380 | 85 | 68 | 6 | 74 | 87 |

TABLE 1-continued

| | Composition of Catalyst | 1 | 2 | 3 | 4 | 5 | 6 | 7 |
|---|---|---|---|---|---|---|---|---|
| 8 | $Mo_{12}Bi_1In_{0.4}Fe_2Ni_8Co_{0.3}P_1O_{51.9}$ | 650° C 20 min. | 390 | 84 | 71 | 5 | 76 | 91 |
| 9 | $Mo_{12}Bi_1In_{0.4}Fe_1Ni_{10}Co_{0.3}W_1P_1O_{53.9}$ | 590° C 10 min. | 390 | 82 | 67 | 6 | 73 | 89 |
| 10 | $Mo_{12}Bi_1In_{0.4}Fe_1Ni_{10}Co_{0.3}W_1P_{0.5}O_{52.7}$ | 650° C 10 min. | 360 | 90 | 64 | 10 | 74 | 82 |
| 11 | $Mo_{12}Bi_1In_{0.4}Fe_1Ni_{10}Co_{0.3}W_1O_{51.4}$ | 650° C 10 min. | 350 | 90 | 60 | 9 | 69 | 77 |
| 12 | $Mo_{12}Bi_1In_{0.4}Fe_3Ni_{2.5}Co_{4.5}W_1P_{0.5}O_{53.9}$ | 650° C 30 min. | 400 | 36 | 30 | 2 | 32 | 89 |
| 13 | $Mo_{12}Bi_1La_{0.05}Fe_1Ni_{10}Co_{0.3}W_{0.5}P_{1.0}O_{53.4}$ | 650° C 20 min. | 356 | 89 | 68 | 6 | 74 | 83 |
| 14 | $Mo_{12}Bi_1La_{0.5}Fe_1Ni_{10}Co_{0.3}W_{0.1}P_1O_{52.9}$ | 590° C 20 min. | 336 | 88 | 71 | 5 | 77 | 88 |
| 15 | $Mo_{12}Bi_1Al_{0.4}Fe_2Ni_8Co_{0.3}W_{0.1}P_1O_{52.2}$ | 590° C 20 min. | 400 | 73 | 55 | 8 | 63 | 86 |
| 16 | $Mo_{12}Bi_1Al_{0.1}Fe_2Ni_8Co_{0.3}W_{0.1}P_1O_{51.8}$ | 600° C 20 min. | 400 | 82 | 66 | 5 | 71 | 87 |
| 17 | $Mo_{12}Bi_1Ga_{0.4}Fe_2Ni_8Co_{0.3}W_{0.1}P_1O_{52.2}$ | 600° C 20 min. | 380 | 88 | 68 | 5 | 73 | 83 |

1 = calcination; 2 = bath temperature in ° C;
3 = conversion of $C_3H_6$; 4 = yield of acrolein;
5 = yield of acrylic acid; 6 = yield of acrolein + acrylic acid
7 = selectivity in respect of acrolein + acrylic acid TABLE 1a

| Comparative experiment | Composition of catalyst | 1 | 2 | 3 | 4 | 5 | 6 | 7 |
|---|---|---|---|---|---|---|---|---|
| 2a | $Mo_{12}Bi_1Fe_1Ni_{10}O_{49}$ | 4 hrs. 486° C | 360 | 90 | 54 | 20 | 74 | 82 |
| 4a | $Mo_{12}Bi_1Fe_{1.2}Co_5W_4O_{56.3}$ | 6 hrs. 470° C | 360 | 79 | 36 | 19 | 55 | 70 |
| 7a | $Mo_{12}Bi_1Fe_1Ni_{10}Co_{0.3}P_1O_{51.8}$ | 10 min. 650° C | 390 | 85 | 57 | 6 | 63 | 70 |

1-7 = same meanings as in Table 1

TABLE 2

| Ex. | Composition of catalyst | 1 | 2 | 3 | 4 | 5 | 6 | 7 |
|---|---|---|---|---|---|---|---|---|
| 18 | $Mo_{12}Bi_1In_{0.4}Fe_{1.2}Ni_8W_{0.5}Sn_{0.6}Cr_{1.2}O_{51.8}$ | 5 hrs. 480° C | 350 | 89 | 73.6 | 6.1 | 79.7 | 89.6 |
| 19 | $Mo_{12}Bi_1In_{0.2}Fe_{1.2}Ni_{0.15}Co_5W_4Mn_{0.6}O_{57.4}$ | 20 min. 600° C | 340 | 85 | 68 | 3 | 71 | 84 |
| 20 | $Mo_{12}Bi_1In_{0.2}Fe_2Ni_8Co_{0.3}W_{0.1}P_1La_{0.2}O_{52.2}$ | 20 min. 600° C | 380 | 89 | 71.1 | 5 | 76.5 | 86 |
| 21 | $Mo_{12}Bi_1In_{0.2}Fe_2Ni_8Co_{0.3}W_{0.1}P_1Pb_{0.3}O_{52.2}$ | 20 min. 600° C | 400 | 70 | 56.5 | 5 | 62.5 | 89.5 |
| 22 | $Mo_{12}Bi_1In_{0.2}Fe_2Ni_8Co_{0.3}W_{0.1}P_1Cu_{0.3}O_{52.2}$ | 20 min. 600° C | 350 | 81 | 67.1 | 5.5 | 72.6 | 90 |
| 23 | $Mo_{12}Bi_1In_{0.2}Fe_2Ni_8Co_{0.3}W_{0.1}P_1Ag_{0.2}O_{52.1}$ | 20 min. 600° C | 350 | 84 | 65.7 | 6 | 71.7 | 85 |
| 24 | $Mo_{12}Bi_1In_{0.2}Fe_2Ni_8Co_{0.3}W_{0.1}O_1Ag_1O_{52.9}$ | 20 min. 600° C | 400 | 0 | 0 | 0 | 0 | 0 |
| 25 | $Mo_{12}Bi_1In_{0.4}Fe_{1.2}Ni_8W_{0.5}Ge_{0.6}Cr_{1.2}O_{51.8}$ | 5 hrs. 480° C | 350 | 90 | 75 | 5.5 | 80.5 | 89.5 |
| 26 | $Mo_{12}Bi_1In_{0.2}Fe_2Ni_8Co_{0.3}W_{0.1}B_1O_{50.9}$ | 20 min. 600° C | 330 | 90 | 71.6 | 5.2 | 76.8 | 85.5 |
| 27 | $Mo_{12}Bi_1In_{0.2}Fe_2Ni_8Co_{0.3}W_{0.1}As_1O_{51.9}$ | 6 hrs. 440° C | 340 | 93 | 72 | 4 | 76 | 82 |
| 28 | $Mo_{12}Bi_1In_{0.2}Fe_2Ni_8Co_{0.3}W_{0.1}P_1Al_{0.1}O_{52.1}$ | 20 min. 600° C | 350 | 91 | 74.2 | 6 | 80.2 | 88 |
| 29 | $Mo_{12}Bi_1In_{0.2}Fe_2Ni_8Co_{0.3}W_{0.1}V_{0.5}O_{50.7}$ | 20 min. 500° C | 350 | 79 | 50 | 9 | 59 | 75 |

1-7 = same as in Table 1

TABLE 3

| Test period in hours | 2 | 3 | 4 | 5 | 6 | 7 |
|---|---|---|---|---|---|---|
| 12 | 380 | 83 | 72 | 2 | 74 | 89 |
| 108 | 380 | 83 | 73 | 3 | 76 | 91.5 |
| 132 | 390 | 85 | 73 | 4 | 77 | 90.7 |
| 156 | 390 | 87 | 74 | 4 | 78 | 89.6 |

TABLE 4

| Test period in hours | 2 | 3 | 4 | 5 | 6 | 7 |
|---|---|---|---|---|---|---|
| 12 | 370 | 87 | 71 | 5 | 76 | 90.6 |
| 24 | 370 | 82 | 68 | 6 | 74 | 90.2 |
| 48 | 390 | 86 | 68.8 | 7.8 | 76.6 | 89 |
| 72 | 390 | 83 | 65 | 8 | 73 | 88 |

2-7 = the same as in Table 1

We claim:
1. A process for the oxidation of an α-olefinic hydrocarbon containing three to four carbon atoms in the gas phase with molecular oxygen to form an α-β-olefinically unsaturated carboxylic acid containing three to four carbon atoms, said process comprising passing a gas mixture of said α-olefinic hydrocarbon, molecular oxygen and an inert gas at a temperature of from 280° to 450° C. over a catalyst consisting essentially of the forumula:

$$Mo_a Bi_b Me^1_c Me^2_d Me^3_e Me^4_f Me^5_g O_h$$

in which:
- $Me^1$ is at least one metal selected from the group consisting of In and La;
- $Me^2$ is at least one metal selected from the group consisting of Fe and Cu;
- $Me^3$ is Ni;
- $Me^4$ is at least one element selected from the group consisting of P, B, As, Cr, V and W;
- $Me^5$ is at least one metal selected from the group consisting of Ag, Pb, Mn, Re, Sn, Ge, Sm, Nb, Ta, Mg, Ca, Sr, Ba and Be;
- $a$ is 12;
- $b$ is 0.1 to 6;
- $c$ is 0.005 to 3;
- $d$ is 0.1 to 8;
- $e$ is 4 to 12;
- $f$ is 0 to 6;
- $g$ is 0 to 3; and
- $h$ is 36 to 102.

2. A process as claimed in claim 1 wherein: $d$ is 0.5 to 3; and $e$ is 6 to 11.

3. A process as claimed in claim 1 wherein $Me^2$ is iron.

4. A process as claimed in claim 1 wherein $Me^4$ is a combination of P + W or Cr + W.

5. A process as claimed in claim 1 wherein: $c$ is 0.01 to 2; $d$ is 0.3 to 6; $e$ is 4 to 12; $f$ is 0.1 to 5; and $g$ is 0.05 to 2.

6. A process as claimed in claim 1 wherein: $b$ is 0.5 to 3; $c$ is 0.01 to 1; $d$ is 0.5 to 3; $e$ is 6 to 11; $f$ is 0.2 to 3; $g$ is 0.1 to 1; and $h$ is 41 to 84.

7. A process as claimed in claim 1 wherein: $Me^2$ is Fe or Fe + Cu and $d$ is 0.5 to 3; $Me^4$ is at least one element selected from the group consisting of P, W and Cr and $f$ is 0.1 to 5; $g$ is 0 and $h$ is 41 to 87.

8. A process as claimed in claim 7 wherein $f$ is 0.2 to 3.

9. A process as claimed in claim 1 wherein: $Me^2$ is Fe and $d$ is 0.5 to 3; $Me^4$ is at least one element selected from the group consisting of P, W and Cr and $f$ is 0.1 to 5; $Me^5$ is an element selected from the group consisting of Sn, Ge, Mn and Re and $g$ is 0.05 to 2; and $h$ is 41 to 84.

10. A process as claimed in claim 9 wherein: $f$ is 0.2 to 3; $g$ is 0.1 to 1; and $h$ is 41 to 76.

11. A process as claimed in claim 1 wherein the gas mixture contains steam.

12. A process as claimed in claim 11 wherein the gas mixture contains up to about 40% by volume of steam.

13. A process as claimed in claim 12 wherein the gas mixture contains less than 10% by volume of steam.

14. A process as claimed in claim 1 wherein the temperature is 300° C. to 420° C. with a residence time of the gas mixture in contact with the catalyst of about 0.05 to 6 seconds.

15. A process as claimed in claim 14 wherein the gas mixture comprises about 0.5 to 15% by volume of the α-olefinic hydrocarbon and about 2 to 20% by volume of oxygen.

16. A process as claimed in claim 15 wherein the gas mixture consists essentially of oxygen, α-olefinic hydrocarbon and inert gases.

17. A process as claimed in claim 15 wherein the gas mixture also contains about 2 to 8% by volume of steam.

* * * * *